US00PP08704P

United States Patent [19]

Machin

[11] Patent Number: Plant 8,704

[45] Date of Patent: Apr. 26, 1994

[54] CHRYSANTHEMUM PLANT NAMED YELLOW SHEENA

[75] Inventor: Barrie J. Machin, Hants, England

[73] Assignee: Goldstock Breeding Limited, Hants, England

[21] Appl. No.: 966,084

[22] Filed: Oct. 23, 1992

[51] Int. Cl.[5] ..... A01H 5/00

[52] U.S. Cl. ..... Plt./78

[58] Field of Search ..... Plt. 76, 78, 82.2

[56] References Cited

U.S. PATENT DOCUMENTS 4,616,099 10/1986 Sparkes ..... 47/58

OTHER PUBLICATIONS

Broertjes, et al., 1980, "Amutant of a mutant of a . . . Irradiation of Progressive Radiation-Induced mutants in a mutation breeding programme with *C. morifolium*", Euphytica, 29:526-530.

Gosling, ed., 1979, "The Chrysanthemum Manual-6th edition", The National Chrysanthemum Society, London, Essex Telegraph Press, Ltd., pp. 329-336.

Broertjes et al., 1978, "Application of Mutation Breeding Methods in the Improvement of Vegetatively Propagated Crops", Elsevier Sci. Pub. Co., New York, pp. 162-175.

Searle, et al., 1968, "Chrysanthemums the Year Round", Blanford Press, London, pp. 27-29, 320-327.

Chan, 1966, "Chrysanthemum and rose mutations induced by X-rays", Am. Sco. Hort. Sci. Proc., pp. 613-620.

Broertjes, 1966, "Mutation breeding of Chrysanthumums", Euphytica, 15:156-162.

*Primary Examiner*—Howard J. Locker

*Attorney, Agent, or Firm*—Foley & Lardner

[57] ABSTRACT

A Chrysanthemum plant named Yellow Sheena, particularly characterized by its straight quill shaped bright yellow ray florets, strong stems, dark green leaves; diameter across the face of the capitulum 84-91 mm when fully opened, when grown as a single stem cut mum; flowering response under normal temperatures of 56-60 days after start of short days; plant height of 80-83 cm when grown with 14 long days prior to start of short days; peduncle length of the first lateral at flowering of 5-14 cm and at the fourth lateral of 10-15 cm, and its terminal spray formation.

3 Drawing Sheets

The present invention comprises a new and distinct cultivar of Chrysanthemum, botanically known as *Dendranthema grandiflora*, and referred to by the cultivar name Yellow Sheena.

Yellow Sheena was discovered by the inventor, Barrie J. Machin, in Fareham, United Kingdom (U.K.) in 1986, as one flowering plant resulting from an induced mutation program. The parent irradiated cultivar was Sheena, a cultivar of Barrie J. Machin, disclosed in pending application Ser. No. 07/965,718.

The female parent of Sheena was a seedling known as Super White, described as a cut spray mum, spider type, having white ray florets, diameter of capitulum 89-90 mm when fully open, a flowering response to short days of 69-63 days, a plant height of 91-109 cm when grown with 14 long days prior to start of short days, a peduncle length of the first lateral of 10-15 cm and of the fourth lateral of 17-22 cm, and a terminal spray formation. The above characteristics are based on plants grown in Fareham, U.K.

The male parent of Sheena was a seedling identified as Dark Westland, disclosed in U.S. Plant Pat. No. 4,967 and described as a cut spray mum, spider type, having deep mauve pink ray florets, diameter of capitulum of 75-84 mm, a flowering response of 56 days, a plant height ranging from 86-96 cm when grown with 14 longs days prior to start of short days, a peduncle length of the first lateral of 10-15 cm and of the fourth lateral of 17-22 cm, and a terminal spray formation. The above characteristics are based on plants grown in Fareham, U.K.

Yellow Sheena was discovered and selected as one flowering plant within the irradiated population by Barrie J. Machin in 1986 in a controlled environment in Fareham, U.K.

In the induced mutation program resulting in Yellow Sheena, cuttings of the parent cultivar Sheena were subjected to irradiation at the level of 1500 rads. Yellow Sheena was discovered by virtue of its pure bright yellow ray floret color, compared to the yellow white ray floret color, with yellow center, of Sheena.

The first act of asexual reproduction of Yellow Sheena was accomplished when vegetative cuttings were taken from the initial selection in Sep. 1986 in a controlled environment in Fareham, U.K. by Barrie J. Machin.

Horticultural examination of controlled flowerings of successive plantings has shown that the unique combination of characteristics as herein disclosed for Yellow Sheena are firmly fixed and are retained through successive generations of asexual reproduction.

Yellow Sheena has not been observed under all possible environmental conditions. The phenotype may vary with variations in environment such as temperature, light intensity and daylength without, however, any variance in the genotype.

The following observations, measurements and comparisons describe plants grown in Fareham, U.K. under greenhouse conditions which approximate those generally used in commercial greenhouse practice.

The following traits have been repeatedly observed and are determined to be basic characteristics of Yellow Sheena which in combination distinguish this Chrysanthemum as a new and distinct cultivar:

1. Quill form.

2. Generally flat flower comprised essentially of ray florets.

3. Bright yellow ray floret color.

4. Diameter across face of capitulum of 84–91 mm when fully opened, when grown as a single stem and spray mum.

5. Flowering response under normal temperatures is 56–60 days after start of short days.

6. Plant height is 80–83 cm when grown with 14 long days prior to short days.

7. Peduncle length of the first lateral at flowering after removing the apical bud without a growth regulator application is 5–10 cm; peduncle length of the fourth lateral at flowering is 10–15 cm; peduncles are strong.

8. Terminal spray formation.

The accompanying color photographic drawings show typical inflorescence and leaf characteristics of Yellow Sheena, with the colors being as nearly true as possible with illustrations of this type.

Sheet 1 is a color photograph of Yellow Sheena grown as a single stem spray cut mum.

Sheet 2 is a black and white photograph of three views of the inflorescence of Yellow Sheena.

Sheet 3 is a black and white photograph showing the upper side of the leaves of Yellow Sheena at three stages of development (mature, intermediate and immature).

Yellow Sheena is similar in many respects to the parent cultivar Sheena. The difference are that Yellow Sheena has pure bright yellow ray floret color (compared to yellow white ray florets with yellow center of Sheena), slightly shorter and more upright laterals, slightly shorter plant height, and a less widely branching spray form. The last noted difference is due to the shorter laterals of Yellow Sheena.

Yellow Sheena can also be compared to the cultivar identified as Super Yellow. Reference is made to attached Chart A which compares certain characteristics of Yellow Sheena to the same characteristics of Super Yellow. Similar traits are capitulum type and spray formation. The ray floret color of Yellow Sheena is pure bright yellow. Also, Yellow Sheena has strong, straight quill shaped ray florets whereas the ray florets of Super Yellow are open and curved at the ends.

In the following description color references are made to The Royal Horticultural Society Colour Chart. The color values were determined on plant material grown as a single cut mum in Fareham, U.K. on Aug. 11, 1988.

Classification:

*Botanical.*—*Dendranthema Grandiflora* cv Yellow Sheena.

*Commercial.*—Quill spray cut mum.

INFLORESCENCE

A. Capitulum:

*Form.*—Quill with all petals being rolled their entire length; a variable number of outer petals have a hole or opening (⅛" or more in diameter) on the upper surfaces near the tips.

*Type.*—Generally flat comprised essentially of ray florets; relatively low profile.

*Diameter across face.*—84–91 mm.

B. Corolla of ray florets:

*Color (general tonality from a distance of three meters).*—Bright yellow.

*Color (upper surface).*—R.H.S. 8B.

*Color (under surface).*—R.H.S. 8B.

*Shape.*—Quill, straight.

C. Reproductive organs:

*Androecium.*—There are few disc florets and thus very low pollen.

*Gynoecium.*—Present in all. Stigmata develop 3–4 days after pollen production.

PLANT

A. General appearance:

*Height.*—80–83 cm.

B. Foliage:

*Color (upper surface).*—R.H.S. 137A.

*Color (under surface).*—Slightly lighter thane R.H.S. 137A.

*Shape.*—See photograph.

CHART A

Comparison of Yellow Sheena and Super Yellow

| Characteristics | Yellow Sheena | Super Yellow |
|---|---|---|
| Ray floret color | Yellow | Yellow |
| Capitulum form | Quill | Spider |
| Diameter across face of capitulum | 89–91 mm | 89–99 mm |
| Flowering response | 56–60 days | 60–63 days |
| Plant height given 14 long days | 86–96 cm | 91–101 cm |
| Peduncle length: | | |
| First lateral | 5–10 cm | 10–15 cm |
| Fourth lateral | 10–15 cm | 17–22 cm |
| Spray form | Terminal | Terminal |

COMPARISONS OF PLANTS GROWN AS SINGLE SPRAY STEM CUT MUMS IN FAREHAM, U.K.

I claim:

1. A new and distinct Chrysanthemum plant named Yellow Sheena, as described and illustrated.

* * * * *

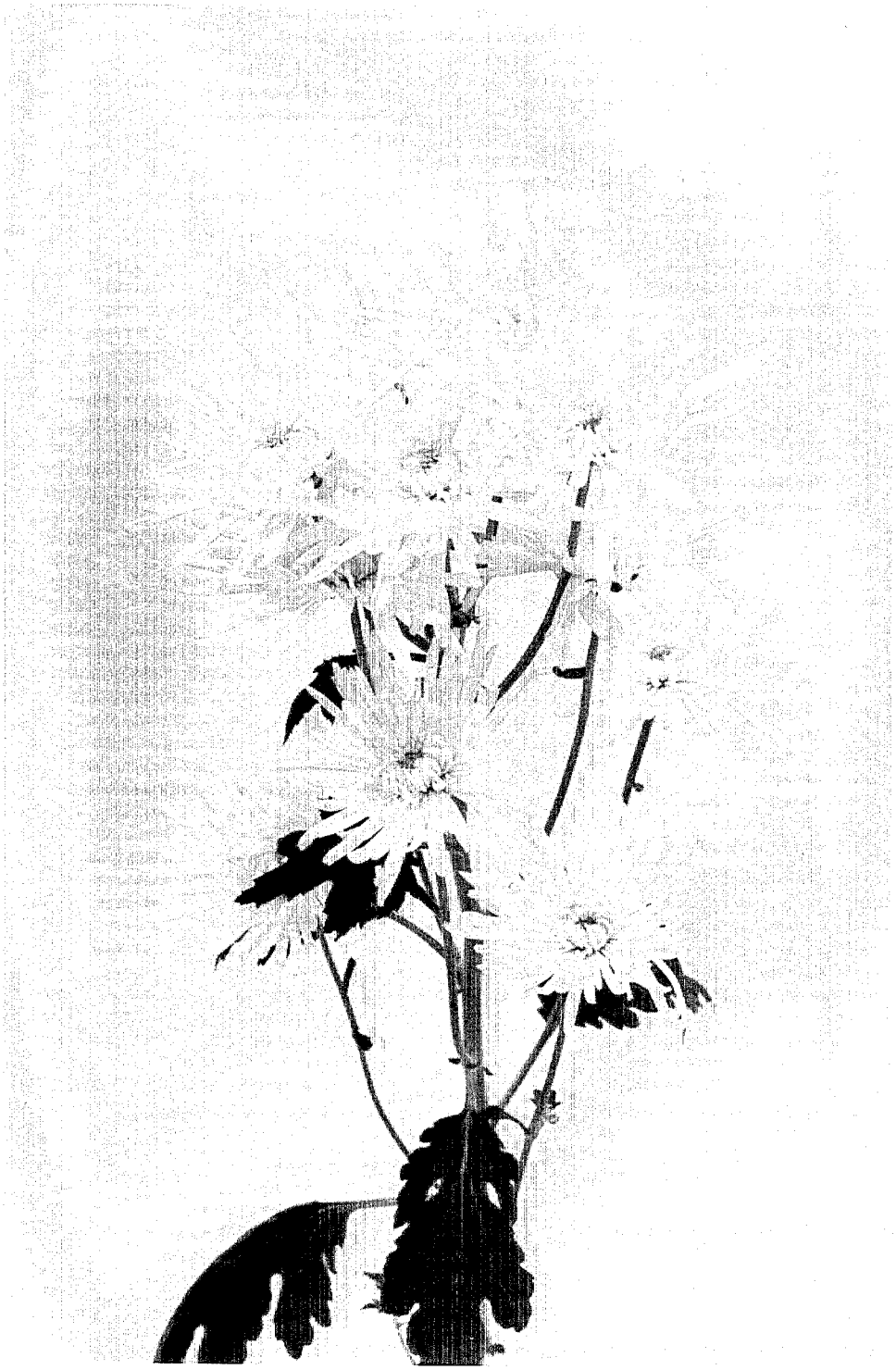

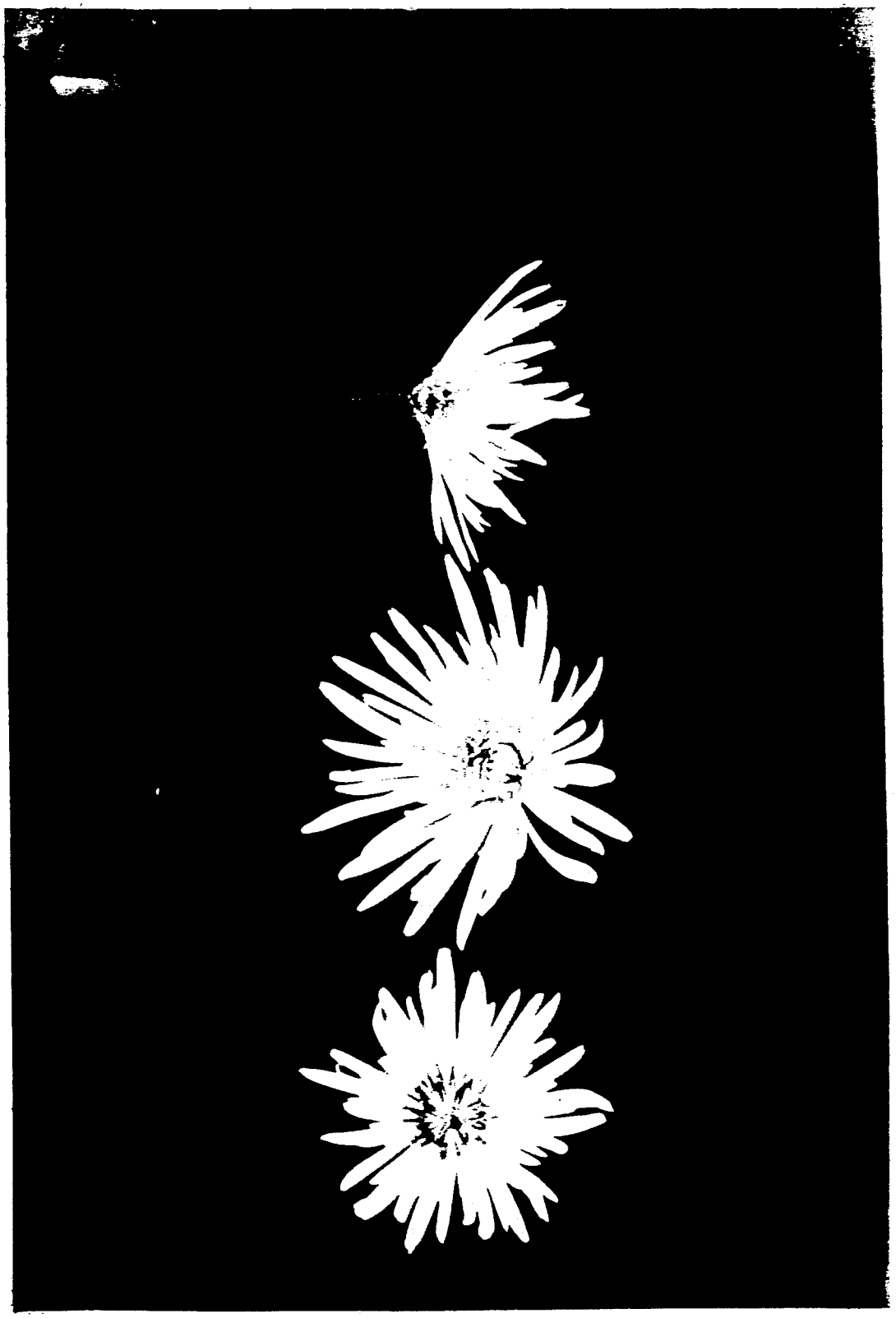

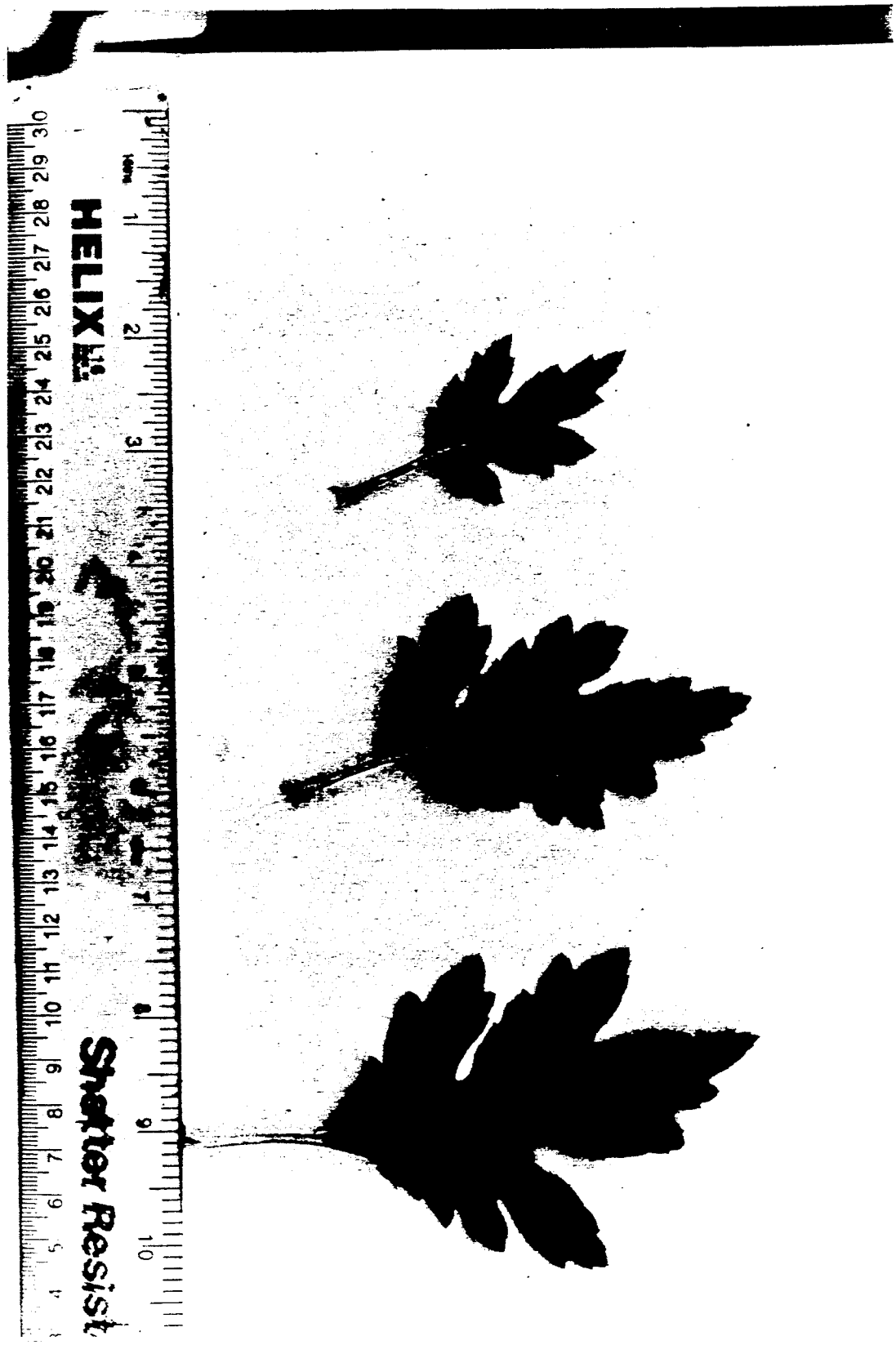
HELIX
Shatter Resist